United States Patent [19]

Colclough et al.

[11] Patent Number: 5,064,886

[45] Date of Patent: Nov. 12, 1991

[54] DITHIOPHOSPHONATES, THEIR PREPARATION AND USE AS ANTI-OXIDANTS

[75] Inventors: Terence Colclough, Abingdon, United Kingdom; Stanley J. Brois, Westfield, N.J.

[73] Assignee: Exxon Chemical Patents Inc., Linden, N.J.

[21] Appl. No.: 452,913

[22] Filed: Dec. 19, 1989

Related U.S. Application Data

[60] Division of Ser. No. 353,187, May 15, 1989, Pat. No. 4,900,852, which is a continuation-in-part of Ser. No. 907,194, Sep. 12, 1986, abandoned.

[30] Foreign Application Priority Data

Sep. 16, 1985 [GB] United Kingdom ................. 8522833

[51] Int. Cl.$^5$ .......................................... C08K 5/5398
[52] U.S. Cl. ..................................... 524/131; 524/132; 524/134; 524/137
[58] Field of Search ............... 524/131, 132, 134, 137; 556/19; 558/194, 133

[56] References Cited

U.S. PATENT DOCUMENTS

| | | | |
|---|---|---|---|
| 3,293,208 | 12/1966 | Millionis et al. | 524/134 |
| 3,310,575 | 3/1967 | Spivack | 524/132 |
| 3,347,790 | 10/1967 | Meinhardt | 558/133 |
| 3,401,185 | 9/1968 | Meinhardt | 524/137 |
| 3,558,747 | 1/1971 | Meltsner | 524/131 |
| 3,801,681 | 4/1974 | Grayson | 524/131 |
| 4,076,690 | 2/1978 | Rosenberger | 558/194 |
| 4,778,840 | 10/1988 | Linhart et al. | 524/131 |
| 4,900,852 | 2/1990 | Colclough et al. | 556/19 |

Primary Examiner—Veronica P. Hoke
Attorney, Agent, or Firm—T. Dean Simmons

[57] ABSTRACT

Certain novel dithiophosphonate derivatives, particularly monoesters, may be prepared inexpensively from hindered phenol compounds and are useful as anti-oxidants for example in lubricants and/or polymer materials.

8 Claims, No Drawings

DITHIOPHOSPHONATES, THEIR PREPARATION AND USE AS ANTI-OXIDANTS

This application is a divisional of application Ser. No. 07/353,187 filed May 15, 1989 now U.S. Pat. No. 4,900,852, which was a C-I-P of application Ser. No. 907,194 filed Sept. 12, 1986 now abandoned.

This invention relates to certain novel dithiophosphonates derived from bindered phenols, a simple method for their preparation and their use as anti-oxidants for example in lubricants and/or plastics materials.

Metal salts of phosphorous acids such as dithiophosphoric acid are well known additives for use in hydrocarbon compositions such as plastics, resins, paints, lubricants, fuels and greases where they are used to promote resistance to degradation due to heat or oxidation. It is desirable for such materials to have good thermal and oxidative stability. Dialkyldithiophosphonates such as the zinc salts of the general formula:

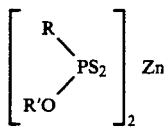  (I)

are known wherein R is an alkyl radical and R' is an alkyl radical or a hydrogen atom. Such compounds have good anti-oxidant activity and better thermal stability than the corresponding dithiophosphate of the general formula:

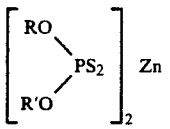  (II)

However, the synthesis of compounds of general formula (I) is expensive and complex which makes them unsuitable for commercial application.

U.S. Pat. No. 3,401,185 describes metal salts of the phosphorus acid of the general formula:

  (III)

wherein one R is selected from the class consisting of hydrocarbon, hydrocarbon-oxy, and XH radicals and the other R is a hydrocarbon radical and X is oxygen or sulphur. In the case where one of the R groups is a hydrocarbon group the salt will be a dithiophosphonate, and example 4 of U.S. Pat. No. 3401185, prepares a phosphonic acid by reaction of phosphorus pentasulphide and polybutylene which is thereafter steam-blown.

It has now been found that a new class of dithiophosphonate derivatives may be prepared simply and show excellent anti-oxidant activity.

Accordingly, in one aspect this invention provides dithiophosphonic acid derivatives of the general formula:

  (IV)

wherein Ar is a hindered phenol group, $R^1$ is a hydrocarbyl radical and $X_1$ is sulphur, oxygen or a group $NR^{11}$ where $R^{11}$ is hydrogen or a hydrocarbyl group. The invention also provides salts of the acid derivatives of general formula (IV) with metals or amines, and S-alkyl derivatives, for example formed with olefinically unsaturated materials such as styrene, diethylmaleate, and isobutylene.

The invention also provides a process for the preparation of the acid derivatives of general formula (IV) in which a thiophosphine sulphide of the general formula:

$$[Ar-PS_2]_2 \quad (V)$$

wherein Ar is as defined hereinbefore) is reacted with an appropriate compound of the formula $R'X_1H$ to form the desired acid of general formula (IV).

The thiophosphine sulphide V may in turn be prepared by reacting the appropriate hindered phenol compound of the general formula ArH with phosphorus pentasulphide. It is a feature of the invention that the group Ar is derived from the class of phenols known as hindered phenols—that is to say, phenols in which the phenyl nucleus is substituted so as to restrict access to the hydroxyl group. Typical of such hindered phenols are the 2,6-di-substituted phenols, particularly where the substituent groups are bulky substituents such as branched alkyl groups. This surprisingly gives the dual advantages of enabling the acid derivative of general formula IV to be prepared by a relatively simple process, and enabling the provision of products which, in the form of salts have shown excellent anti-oxidant activity.

A particularly preferred group of hindered phenols is the 2,6-di-t-alkyl-phenols such as 2,6-di-t-butyl-phenol.

By reacting the hindered phenol compound with phosphorus pentasulphide, the thiophosphine sulphide of general formula (V) is formed. This reaction is preferably carried out in a solvent such as an aromatic hydrocarbon and examples of suitable hydrocarbons include xylenes. The reaction is preferably carried out at elevated temperature, typically at from 60°-250° C., preferably from 100°-200° C., and most preferably in the range of 120°-160° C. The thiophosphine sulphide may be isolated from the reaction mixture by filtration before being used in the following step, but it may also be used directly without any purification.

In the next step the thiophosphine sulphide of general formula (V) is reacted with a compound of the general formula $R'X_1H$. The thiophosphine sulphide may be reacted with an alcohol to form a monoester, a thiol to form a monothioester, or a primary or secondary amine. The compound of general formula $R'X_1H$ is also selected so as to introduce the desired group $R'$ into the acid of general formula (IV). This group $R'$ is a hydrocarbyl group and is preferably an alkyl group having from one to 30 carbon atoms or a phenyl group. The choice of $R'$ is made having regard to the intended function of the product of the invention.

If it is desired to have a liquid product, which is frequently desirable for lubricant applications, R' should be a higher alkyl group having 10 or more carbon atoms preferably 12 or more carbon atoms, to obtain a liquid product with the desired oil solubility. When R' is a lower alkyl group the product will tend to be solid and will be more useful in applications such as compounding with solid organic material such as rubbers and plastics materials.

Suitable higher alcohols with which the thiophosphine sulphide may be reacted are those obtained from oxo reactions carried out on olefins. Commercially available oxo alcohols are generally in the form of mixtures which may also be used satisfactorily in the process of this invention. Preferred alcohol mixtures are $C_{4/5}$ alcohols, $C_{9/10/11}$ alcohols and $C_{12/13}$ alcohols.

In general, the preferred substituents R' in thiols and amines will be chosen with the same considerations in mind.

The reaction is conveniently carried out by slurrying the thiophosphine sulphide with the compound $R'X_1H$, preferably with heating. Typically the reaction mixture is heated to a temperature of 40°–100° C., preferably 50°–80° C.

The formed compound of general formula (IV) may be separated from the reaction mixture, or used as it is for the following step of converting this material into its salt or adduct. Salt formation may be effected by reacting the acid of general formula (IV) with an appropriate basic compound of the selected metal, or with an amine.

S-alkyl derivatives are formed by reacting the acid in a similar manner with the selected unsaturated material, or by reacting a metal salt of the acid with an alkyl halide such as the bromide.

In each case the salt or derivative formation is preferably carried out by warming to an elevated temperature of from 40°–100° C. preferably 50°–80° C. It is possible to use a promoter in the form of a metal salt, where the metal in the promoter is preferably the same as the metal in the salt-forming base.

Preferred salts of the acid derivative of general formula IV, are those formed with metals such as lithium, potassium, sodium, aluminium, barium, calcium, strontium, magnesium, zinc, iron, cobalt, nickel, cadmium or molybdenum, although other alkaline metals, alkaline earth metals and transition metals may be employed. Typically, the basic metal compound will be an oxide, hydroxide, hydride, carbonate, bicarbonate, sulphide, lithoxide, ethoxide or phenoxide of the metal but the most frequently used compounds are the oxides, carbonates and hydroxides of zinc, barium, calcium, cadmium, copper, molybdenum, nickel, cobalt, lithium, sodium or magnesium.

The invention extends to the use of salts and adducts of the acid derivative of general formula IV as anti-oxidants in hydrocarbon compositions, that is to methods of reducing oxidative degradation of such compositions by incorporating effective amounts of such salts and adducts therein. A preferred class of compounds of the invention are the metal salts of the acid derivative of general formula IV wherein Ar is a 2,6-di-t-butylphenol group. The phenol itself is a known anti-oxidant and it is a surprising feature of the invention that salts of this compound have particularly remarkable anti-oxidant activity as well as offering advantages in other areas which may include anti-wear and corrosion inhibition properties in lubricant compositions.

The materials of this preferred class are useful in oxidation and light stabilization of plastics materials, in particular homopolymers and copolymers based on ethylene and/or propylene.

The metal salts chosen may also be dictated by end use of the material. Zinc and copper salts, as well as alkaline metal and alkaline earth metal salts, may be particularly useful in lubricant compositions, while transition metal salts and particularly nickel salts may be useful in anti-oxidants for plastics materials.

When the salts of the acid derivatives of general formula IV are used in lubricant compositions they are usually present in an amount of from 0.01 to 10 wt % of the total lubricant composition, preferably from 0.1 to 5 et %. The lubricating oil in which they are used may be any suitable mineral or synthetic oil with lubricating viscosity which would normally be selected according to the use of the lubricant. The salts of the invention will normally first be formed into an additive concentrate in the form of an oil solution containing 10 to 90 wt % of the salt of the invention in a lubricating oil, which may be diluted with further oil to form a lubricating composition. The diluent in such concentrates may be any inert diluent, but is normally a lubricating oil to facilitate mixture to form a lubricant composition.

Other additives may be present in the concentrates or lubricating formulations and these additives includes detergents, inhibitors, anti-rust additives, foam inhibitors, corrosion inhibitors, metal deactivators, pour point depressants, anti-wear additives, anti-oxidants, dispersants, viscosity index improvers, surfactants, demulsifiers and copper corrosion inhibitors/sulphur scavengers such as trialkyl and triaryl phosphites, thiadiazoles and benzotriazoles. It is believed to be within the competence of one skilled in the art to select appropriate additives for a lubricant composition. However, it is believed that the compounds of the invention are particularly suitable for use in lubricant additives and provide particularly effective antioxidant properties.

When used in other hydrocarbon polymer compositions such as plastics (e.g. polypropylene, polyethylene) and rubbers (e.g. ethylene-propylene copolymers and EPDM terpolymers), the salts and adducts of the invention will typically be employed at a rate of 0.1 to 50 wt % of the hydrocarbon composition, preferably from 0.1 to 10 wt % of the composition. However, it is frequently convenient to use the salt or adducts of the invention in a master batch or concentrate in which it is present in an amount from 10 to 90 wt % in combination with a solid diluent material such as the hydrocarbon in which it will ultimately be used. Such master batches can then be readily formulated into the finished hydrocarbon composition:

The following examples and test results illustrate the invention.

EXAMPLE 1

Preparation of dithiophosphonates from 2,6-di-t-butylphenol (i) Preparation of Dithiophosphonic Acid 2,6-di-t-butylphenol (675 g, 3.3 moles) and $P_2S_5$ (333 g, 1.5 moles) were heated in xylene (400 ml) at 140° C. for 3.5 hours, by which time 51.2 g $H_2S$ (100% had been evolved. The reaction mixture was cooled to 70° C. and tridecanol (635 g, 3.2 moles) added over 45 mins. Heating was continued for a further 1.5 hrs at 70° C. The reaction mixture was cooled and a grey solid (47 g Found P, 23.0; S, 60.42) was filtered off. The filtrate (1540 g) had TAN=86 mgKOH/g (Theory 112 mg KOH/g).

(ii) Preparation of Zinc Salt

The crude dithiophosphonic acid (1539 g) was added over 6 hours to a slurry of ZnO (121 g, 25%, excess) and $ZnCl_2$ (3 g) in diluent oil (200 g) at 70° C. The reaction mixture was allowed to heat soak for 1 hour at 70° C. then allowed to stand 16 hours. Filtration through Special Speedflow and Superaid gave 1644 g zinc salt (92%). A further 440 g of diluent oil was added to give a 70% a.i. product (Found: Zn, 4.9; P, 4.1; A; Zn/P=1.19.

(iii) Preparation of Tri-n-butylamine Salt

The crude dithiophosphonic acid was reacted with tri-n-butylamine under conditions similar to those as described for step (ii) to form the amine salt.

(iv) Preparation of Copper Salt

The copper salt was prepared by reacting the crude dithiophosphonic acid with cuprous oxide under similar conditions, as described for step (ii).

EXAMPLE 2

Preparation of 4-[2,6-di-t-butylphenol]-Thiophosphine Sulphide (TPS)

$P_2S_5$(110 g), 2,6-di-t-butylphenol (206 g) and chlorobenzene (300 cm³) were heated to 155° C. under nitrogen for 6 hours with stirring. On cooling, yellow 2,6-di-t-butylphenol thiophosphine sulphide crystallised out (yield=88%)

EXAMPLE 3

Preparation of Amino Derivative 30.7 g of the product of Example 2 and 15.4 g of n-butylamine were added to toluene (200 ml), and heated to 50° C. for 1 hour. The product was recovered by stripping off the toluene.

EXAMPLE 4

Reaction of TPS with Alcohol

Isobutanol (11 g) was added to the product of Example 2 (40 g) in chlorobenzene (300 cm³) as solvent under nitrogen at 70° C. After the mixture was soaked at 70° C. for 1.5 hours the chlorobenzene was removed giving a white solid (95% yield) of the formula:

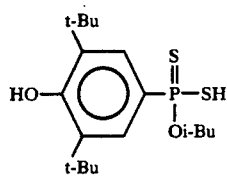

referred to herein as i-BuDTPA

EXAMPLE 5

Preparation of $NH_4$ Salt

The acid formed in Example 4 was dissolved in chlorobenzene (xylene or toluene can also be used) and $NH_3$ gas was bubbled through for 20 minutes. A white solid crystallised out in 100% yield of the formula:

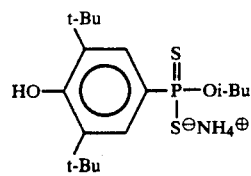

EXAMPLE 6

Preparation of Copper Dithiophosphonate

Cuprous oxide (10.9 g, 1.7 mols) was added slowly to the I-Bu DTPA (30 g 1 mol) in chlorobenzene (250 cm³) at 80° C. After 2 hour heat soak, the solution was cooled and unreacted CuO filtered off. Chlorobenzene was removed on a rotary evaporator. An orange coloured oil remained which was treated with methanol to give a yellow solid (40% yield) of the formula:

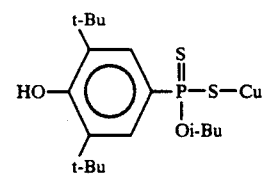

EXAMPLE 7

Preparation of a Trithiosphosphonic Acid and its Complexes with Copper

TPS (50 g) as prepared in Example 2 was dissolved in xylene (200 cm³) under nitrogen and heated to 100° C. Thiophenol (18.5 g, 2 mols) was added dropwise. The mixture was heat-soaked for one hour when the colour changed from yellow to colourless. The solution was filtered and the trithiophosphonic acid recrystallised.

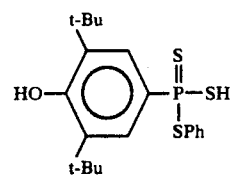

Analysis: Found C% 59.6 H% 6.48
Theory C% 58.5 H% 6.58

The acid was dissolved in xylene and $NB_3$ gas bubbled through for 20 minutes. The ammonium salt was formed as white precipitate and filtered.

$CuCl_2$ was dissolved in water and added to a suspension of the ammonium salt in xylene. A yellow solid floated to the top of the aqueous phase and was filtered, washed with water and methanol and dried to yield the copper salt of the trithiophosphonic acid.

Test Results

A test lubricating oil was prepared containing a major amount of a mineral lubricating oil and 4.5 wt % of a dispersant concentrate comprising a polyisobutenyl succinic anhydride reacted with polyethylene amine and then borated, and 1.0 wt % of a 400 TBN (Total Base Number) magnesium sulphonate containing 9.2 wt % magnesium. To this was added a compound of the invention in an amount such as to give a phosphorus level of 0.05 wt % in the lubricating oil composition—unless otherwise stated. The oxidation stability of this oil composition further containing 40 parts per million of iron as ferric acetylacetonate was measured by passing 1.7 liters of air per minute through the sample at 165° C. and determining the viscosity at 40° C. intervals up to 4 hours on a Ferranti-Shirley cone-on-plate-viscometer. In this test the oil composition is just about to turn solid at ambient temperature When a viscosity Of about 500 centipoise is reached.

The oxidation stability of the oil composition containing compounds of the invention was compared with oil compositions containing conventional antioxidants including a zinc dialkyl dithiophosphate in which the alkyl groups are a mixture of $C_4$ and $C_5$ alkyl radicals prepared by reacting $P_2S_5$ with a mixture of about 65% isobutyl alcohol and 35% amyl alcohol (hereinafter referred to as "ZDDP") and a commercially available hindered phenol Ethyl 702, available from Ethyl Corporation. The results are given in the following tables.

TABLE 1

| Antioxidant | Wt % | | | | | |
|---|---|---|---|---|---|---|
| Example 1 (iii) | 1.06 | — | — | — | — | — |
| Example 1 (ii) | — | 0.8 | — | — | — | — |
| Example 1 (iv) | — | — | 0.86 | — | — | — |
| ZDDP | — | — | — | 0.7 | — | 0.7 |
| Ethyl 702 | — | — | — | — | 1.0 | 1.0 |
| Viscosity (CP) at Hours | | | | | | |
| 0 | 38.6 | 35.6 | 35.6 | 36.3 | 35.0 | 37.0 |
| 18 | 67.0 | 106.6 | 39.9 | 103.0 | 73.3 | 47.9 |
| 24 | 123.8 | 202.3 | 48.2 | 203.9 | 141.9 | 100.0 |
| 40 | 495.3 | 236.6 | 114.2 | 1362.8 | 843.0 | 54.9 |
| 48 | 1118.5 | — | 182.5 | — | — | 144.4 |
| 64 | — | — | 283.8 | — | — | — |

TABLE 2

| (Repeat of test reported in Table 1) | | | | |
|---|---|---|---|---|
| Antioxidant | Wt % | | | |
| Example 1 (iii) | 1.06 | — | — | — |
| Example 1 (ii) | — | 0.8 | — | — |
| Example 1 (iv) | — | — | 0.86 | — |
| ZDDP | — | — | — | 0.7 |
| Viscosity (CP) at Hours | | | | |
| 0 | 35.6 | 46.9 | 46.9 | 34.0 |
| 18 | 66.3 | 116.8 | 53.5 | 84.5 |
| 24 | 126.1 | 230.0 | 53.8 | 165.7 |
| 40 | 662.6 | — | 147.2 | 1077.5 |
| 48 | — | — | 202.6 | — |
| 64 | — | — | 205.9 | — |

TABLE 3

| (testing at 0.01 wt % P) (Less Than 30 ppm S, No Other Additives and No Iron Catalyst Present) | | | | |
|---|---|---|---|---|
| Antioxidant | wt % | | | |
| ZDDP | 0.14 | — | — | — |
| Copper salt of an acid similar to Example 1 (i) but prepared with a $C_8$ alcohol in place of $C_{13}$ alcohol | — | 0.16 | — | — |
| Zinc Salt of the acid prepared from $C_8$ alcohol | — | — | 0.15 | — |
| Control | — | — | — | 0 |
| Viscosity (CP) at Hours | | | | |
| 0 | 48 | 44.5 | 46 | 32 |
| 18 | 45 | 61.0 | 44 | 180 |
| 24 | 61 | 81.0 | 50 | 500+ |
| 40 | 64 | 426.5 | 46 | — |
| 48 | 500+ | — | 500+ | — |

(Less Than 30 ppm S, No Other Additives and No Iron Catalyst Present)

We claim:

1. A hydrocarbon polymer composition comprising, as anti-oxidant, a salt or adduct of an acid derivative of general formula IV with a metal or an amine:

(IV)

wherein the anti-oxidant is present in an amount of from 0.1 to 50 wt % of the hydrocarbon composition, Ar is a hindered phenol group, R' is a hydrocarbyl radical and $X_1$ is selected from sulphur, oxygen and group NR" where R" is hydrogen or hydrocarbyl group.

2. A composition as claimed in claim 1, in which the anti-oxidant is an alkyl monester of general formula IV wherein the ester contains less than 10 carbon atoms.

3. A hydrocarbon polymer composition comprising, as anti-oxidant, a salt or adduct of an acid derivative of general formula IV with an amine:

(IV)

wherein the anti-oxidant is present in an amount of from 0.1 to 50 wt % of the hydrocarbon composition, Ar is a hindered phenol group, R' is a hydrocarbyl radical and $X_1$ is selected from sulphur, oxygen and group NR" where R" is hydrogen or hydrocarbyl group.

4. A composition as claimed in claim 3, in which the anti-oxidant is an alkyl monester of general formula IV wherein the ester contains less than 10 carbon atoms.

5. A masterbatch comprising a hydrocarbon polymer material and an antioxidant comprising from 10 to 90 wt % of a salt or adduct of an acid derivative of general formula IV with a metal or an amine:

(IV)

wherein Ar is a hindered phenol group, R' is a hydrocarbyl radical and $X_1$ is selected from sulphur, oxygen and group NR" where R" is hydrogen or hydrocarbyl group.

6. A masterbatch as claimed in claim 5 in which the anti-oxidant is an alkyl monoester of general formula IV wherein the ester contains less than 10 carbon atoms.

7. A masterbatch comprising a hydrocarbon polymer material and an antioxidant comprising from 10 to 90 wt % of a salt or adduct of an acid derivative of general formula IV with an amine:

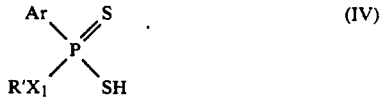

(IV)

wherein Ar is a hindered phenol group, R' is a hydrocarbyl radical and $X_1$ is selected from sulphur, oxygen and group NR" where R" is hydrogen or hydrocarbyl group.

8. A masterbatch as claimed in 7 in which the antioxidant is an alkyl monester of general formula IV wherein the ester contains less than 10 carbon atoms.

* * * * *